United States Patent
Wohlgemuth

(10) Patent No.: US 9,125,690 B2
(45) Date of Patent: Sep. 8, 2015

(54) MEDICAL POSITION DETERMINATION USING REDUNDANT POSITION DETECTION MEANS AND PRIORITY WEIGHTING FOR THE POSITION DETECTION MEANS

(75) Inventor: Richard Wohlgemuth, Bad Tölz (DE)

(73) Assignee: Brainlab AG, Feldkirchen (DE)

( * ) Notice: Subject to any disclaimer, the term of this patent is extended or adjusted under 35 U.S.C. 154(b) by 2364 days.

(21) Appl. No.: 11/747,489

(22) Filed: May 11, 2007

(65) Prior Publication Data

US 2007/0265527 A1 Nov. 15, 2007

Related U.S. Application Data

(60) Provisional application No. 60/747,357, filed on May 16, 2006.

(30) Foreign Application Priority Data

May 11, 2006 (EP) .................................... 06009743

(51) Int. Cl.
*A61B 5/05* (2006.01)
*A61B 17/50* (2006.01)
*A61B 19/00* (2006.01)
*A61B 6/00* (2006.01)
*G05B 9/03* (2006.01)

(52) U.S. Cl.
CPC ............. *A61B 19/5244* (2013.01); *A61B 6/547* (2013.01); *A61B 19/2203* (2013.01); *A61B 19/52* (2013.01); *G05B 9/03* (2013.01); *A61B 2019/5255* (2013.01)

(58) Field of Classification Search
USPC ........................................ 600/424, 426, 423
See application file for complete search history.

(56) References Cited

U.S. PATENT DOCUMENTS

| | | | |
|---|---|---|---|
| 5,086,401 A * | 2/1992 | Glassman et al. | 700/259 |
| 5,394,875 A * | 3/1995 | Lewis et al. | 600/445 |
| 5,724,264 A * | 3/1998 | Rosenberg et al. | 702/152 |
| 5,976,156 A | 11/1999 | Taylor et al. | |
| 5,980,535 A | 11/1999 | Barnett et al. | |
| 6,246,898 B1 | 6/2001 | Vesely et al. | |
| 6,285,902 B1 | 9/2001 | Kienzle, III et al. | |
| 6,288,785 B1 | 9/2001 | Frantz et al. | |

(Continued)

FOREIGN PATENT DOCUMENTS

| | | |
|---|---|---|
| DE | 101 09 310 | 9/2002 |
| DE | 102 25 077 | 12/2003 |

(Continued)

*Primary Examiner* — Joel F Brutus
(74) *Attorney, Agent, or Firm* — Tucker Ellis LLP

(57) ABSTRACT

A device and method for determining a position of a medical device or part of a patient's body uses first and second position detection devices to obtain first and second positions, respectively, of the medical device or part of the patient's body, wherein the first position detection device is separate from the second position detection device. A first priority is assigned to the first position and a second priority is assigned to the second position, wherein the first and second priority are based on at least one input variable, and the first and second priority define a first and second weight factor to be applied to the respective first and second position. The position of the medical device or part of the patient's body is determined from the combination of the first position and the first weight factor, and the second position and the second weight factor.

22 Claims, 1 Drawing Sheet

(56) References Cited

U.S. PATENT DOCUMENTS

| | | |
|---|---|---|
| 6,322,567 B1 | 11/2001 | Mittelstadt et al. |
| 6,424,885 B1 * | 7/2002 | Niemeyer et al. ............ 700/245 |
| 6,547,782 B1 | 4/2003 | Taylor |
| 2001/0011175 A1 | 8/2001 | Hunter et al. |
| 2001/0013764 A1 * | 8/2001 | Blumenkranz et al. .. 318/568.11 |
| 2002/0123825 A1 | 9/2002 | Ohtsuki |
| 2003/0033024 A1 | 2/2003 | Sunaoshi |
| 2003/0055410 A1 * | 3/2003 | Evans et al. ...................... 606/1 |
| 2003/0195526 A1 | 10/2003 | Vilsmeier |
| 2004/0097952 A1 | 5/2004 | Sarin et al. |
| 2004/0260481 A1 | 12/2004 | Heiligensetzer et al. |
| 2005/0024586 A1 | 2/2005 | Teiwes et al. |
| 2005/0113677 A1 | 5/2005 | Davies et al. |

FOREIGN PATENT DOCUMENTS

| | | |
|---|---|---|
| EP | 0 114 505 | 8/1984 |
| EP | 0 456 103 | 11/1991 |
| EP | 0 676 178 | 10/1995 |
| EP | 1 096 268 | 5/2001 |
| EP | 1 219 259 | 7/2002 |
| EP | 1 354 564 | 10/2003 |
| EP | 1 056 572 | 11/2003 |
| EP | 1 445 075 | 8/2004 |
| EP | 1 294 300 | 11/2004 |
| WO | 2004/014244 | 2/2004 |
| WO | 2005/048039 | 5/2005 |

* cited by examiner

MEDICAL POSITION DETERMINATION USING REDUNDANT POSITION DETECTION MEANS AND PRIORITY WEIGHTING FOR THE POSITION DETECTION MEANS

RELATED APPLICATION DATA

This application claims priority of U.S. Provisional Application No. 60/747,357 filed on May 16, 2006, which is incorporated herein by reference in its entirety.

FIELD OF THE INVENTION

The invention relates to medical position determination and, more particularly, to medical position determination using redundant position detection devices, wherein priority weighting is applied to each position detection device.

BACKGROUND OF THE INVENTION

Presently, operating rooms are being increasingly equipped with so called navigation systems. These navigation systems help operating physicians determine a positional relationship between treatment devices (e.g., instruments) and patients or parts of a patient's body. The navigation systems also can provide treatment-assisting image outputs.

In order to provide functioning navigation, it is necessary to determine and track the positions of the treatment devices and/or treatment-assisting devices and the patient in a pre-defined coordinate system. This process is called "tracking". There are optical or magnetic tracking systems that can locate and track reference markers or reference marker arrays, which may be attached to the treatment devices and/or to the patient. However, it is also possible, for example, to position a tracked instrument on other objects or parts of the patient, and then identify the location of the object based on a known location of the instrument. Another type of tracking system can specifically be used for manipulators such as, for example, medical or surgical robots, wherein sensors are coupled to joints of said manipulators. The sensors can ascertain movement of the manipulators and, therefore, movement of an instrument attached to the manipulator (e.g., relative to a pre-calibrated zero position).

Using such position detection devices for redundant position measuring is known. In such systems, for example "external data" obtained via a camera tracking system that tracks reference marker arrays attached to an object of interest can be transformed into a robot coordinate system and used as input data for controlling the robot. The robot, which can include an "internal tracking system", e.g., a joint sensor tracking system, detects its own tracking data, and the redundancy of the joint sensor data and the data of the external tracking system can be used to compensate for a failure of a tracking data source. In this manner, treatment and/or treatment assistance does not have to be interrupted. If the data of the redundant position detection devices do not match, the treatment assistance and/or operation of the robot can be halted, the movement of a joint arm may be stopped, or the operation of an active tool may be discontinued.

A method is known from U.S. Pat. No. 6,547,782 B1 that limits the movement of an instrument attached to a robot within a patient to a predetermined plan. The use of redundant joint sensors is disclosed.

EP 0 456 103 A3 and/or U.S. Pat. No. 5,086,401 disclose a method for a redundant consistency check on a surgical robot, with position control of a tool and safety monitoring of the position of the tool by a camera system. The operational status is periodically monitored, and means are provided for preventing further movement of the tool when the operational status is not optimum.

Redundant position detection has thus hitherto been used to improve the safety of automatic or guided treatment procedures by halting the treatment in different detected positions or replacing one position data source with another position data source when the first fails.

SUMMARY OF THE INVENTION

A method for determining the position of a medical device or part of a patient's body is provided. The method can include:
  a) detecting at least two positions (e.g., a first and second detected position) for the device or part of the body using separate position detection means;
  b) on the basis of at least one defined input variable, the respective detected positions are assigned a particular priority that defines a weighting of the respective detected positions in the position determination; and wherein
  c) the position determination is made from a combination of the detected positions by taking into account the weighting of the respective detected positions.

Thus, the obtained position data from the redundant systems are not simply "taken at face value", but rather the position information is evaluated. Redundant position data are assigned a priority so as to determine the weighting of the position data on the basis of the priority and to calculate a position on the basis of the weighted redundant positions. This calculated position then can be used as input data for medical treatment. The method thus increases the safety and accuracy of the navigation-assisted treatment, since, for the first time, it takes into consideration the fact that the reliability and accuracy of position data can change during a treatment (e.g., due to external influences, etc.). Since these external influences can have different effects on the reliability and accuracy of different tracking devices, it is precisely the reliability and accuracy over the total period of time of treatment that is optimized by the method proposed herein.

This also optimizes as a whole the use of data obtained from various position detection devices (which can be identical or different in nature) since, in contrast to the prior art, one data source is not simply preferred as a standard and the information from the other data source neglected. Through weighting and prioritizing, it is possible to use position information from multiple detection devices, even if they are intentionally different.

The respective detected positions are preferably made for a point in time, in particular for the same point in time, within the course of the treatment. The weighting of the respective detected positions can be greater than 0% and less than 100%.

Input variable(s) describe in particular the reliability and/or accuracy of the respective detected position, and the input variables can include external parameters and/or predefined priority rules. Embodiments of the method are presented in which the input variables(s) include at least one of the following variables:
  a) the distance measured between a medical device and a part of the body;
  b) the time interval since the last calibration of a respective position detection device;
  c) the current detectability of a respective position detection device;
  d) the difference between the positions detected by the respective position detection devices;

e) the calculation of the ratio between the priority of one position detection device and another position detection device, the priority of which is constant;

f) an average or interim value of the detected positions.

When the distance measured between a medical device and a part of the body is used as an input variable, any distance or range of distances can be assigned a specific priority. When the time interval since the last calibration of a respective position detection device is used as an input variable, the reference position can be provided by one of the position detection devices, for example, by moving a functional element of a selected position detection device to the device and/or part of the body that is to be positionally determined (e.g., the tip of a tracked instrument). Calibration, among other things, also can be understood to mean that a first position detection device that does not know the position of a patient (e.g., jointed robot) is initially sent the location of the patient relative to the first position detection device by a second position detection device.

Other control variables also can be taken into account in position determination. These control variables, for example, can be taken into account based on a request obtained via user inputs, user confirmations or interventions in position determination by the user, in particular user override inputs.

It is possible to restrict the priority of a position detection to a particular time interval. The priorities assigned can be recorded in the system so as to enable reference to the priorities at a later time.

In one specific embodiment, one of the position detection devices may be a medical manipulator, in particular a medical or surgical jointed robot, and another position detection device may be an optical or magnetic medical tracking system. The input variable(s) may include at least one of the following variables:

a) the number of reference markings detected by the tracking system, specifically the number of detected markings within a group or array of reference markings and/or the quality of detection;

b) the difference between position data from at least two redundant joint position sensors of the robot;

c) forces which are measured by force sensors on the robot;

d) the difference between position data from the jointed robot and from the tracking system;

e) the position of the tracking reference markings in the field of vision of the tracking system;

f) when the robot base is tracked by the tracking system, the distance and/or change in distance over time between the base and the medical device/part of the body.

Redundant position data and assigned priorities can be exchanged between multiple robots. The priority of the position data for one robot then can be determined as a function of the priority settings of at least one other robot.

A method for controlling a medical manipulator, such as a medical (surgical) robot, is also provided, wherein the manipulator may be controlled with the aid of position information obtained using a position determining method such as has been described herein in various embodiments. The position information from the position determining method then can serve as input data for the manipulator, so that the manipulator may be optimally moved to the treatment target, wherein the position data having the highest priority or improved position information calculated from the redundant data can be used. In this specific case, the utilized position data may be a particular function of the redundant position data and the assigned priority. The position input data for controlling the manipulator/robot can be changed if the priority is changed; the position input data also can be changed by user intervention. In one embodiment, the position input data are only changed when the difference between various position detection data reaches or exceeds a threshold value.

It is possible to display the weighting of the detected positions to the user by means of a signal output. On the one hand, this can be achieved optically, for example, by screen displays or display lights, or on the other hand by different audio outputs.

Also provided herein is a program which, when it is running on a computer or is loaded onto a computer, causes the computer to perform a method such as has been described above in various embodiments, and a computer program storage medium comprising such a program.

A device for determining the position of a medical device or of a part of a patient's body has at least two separate position detection means or devices for detecting the position of the medical device or part of the body, and can comprise a controlling and data processing unit that includes a memory unit and/or input unit for at least one defined input variable. On the basis of the at least one defined input variable, the respective detected positions may be assigned a particular priority that defines the weighting of the respective detected positions in the position determination, wherein the position of the medical device or part of the body is then determined by the controlling and data processing unit from a combination of the detected positions, taking into account the weighting of the respective detected positions.

A control device for a medical manipulator, such as a medical robot (surgical robot) that is controlled with the aid of position information, is provided with a position determining device such as described herein. The position determining device and the control device can of course contain all the components and elements that have been described in more detail above in relation to the method, and which fulfill the corresponding functions.

BRIEF DESCRIPTION OF THE DRAWINGS

The forgoing and other features of the invention are hereinafter discussed with reference to the drawings.

DETAILED DESCRIPTION

Figure 1:
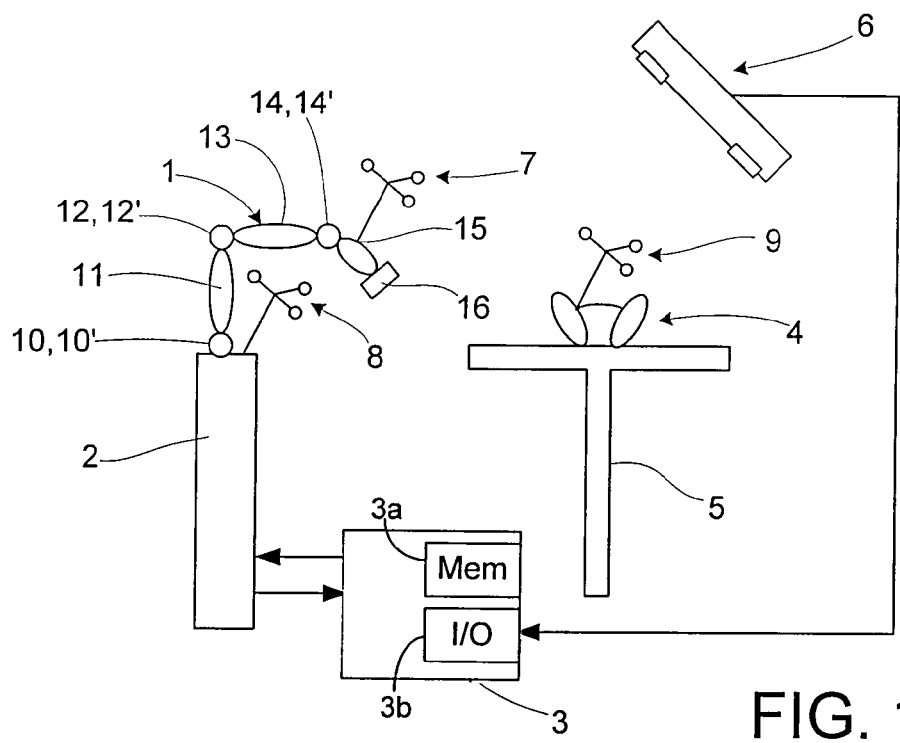
FIG. 1 is a schematic diagram of an exemplary redundant tracking setup in accordance with the invention.

FIG. 1 shows an exemplary setup for a medical treatment room in which a surgical robot 1 is placed on its base 2. Starting from its base, the robot 1 includes a first joint 10 including a joint position sensor 10', to which a first arm part 11 is connected, which is in turn followed by a joint 12 including a joint position sensor 12'. Attached to the joint 12 is the second arm part 13, which is then followed by a third joint 14 and joint position sensor 14', which in turn bears the third arm part 15. A functional component 16 is schematically shown attached to a front of the third arm part 15 and, thus the functional component 16 may be manipulated by the robot 1. It is possible to use robots with at least one or also with more than three joints (for example, seven joints). The base 2 of the robot 1 may be provided with a reference array 8 that includes three reference markers; similarly, the third arm part 15, which is non-movable relative to the functional element 16, may be equipped with a corresponding reference array 7. The reference array 7 also can be directly arranged on an instrument that is held by the robot (or by the functional element).

FIG. 1 also shows a patient table 5 on which a patient 4 is lying. A reference array 9 is attached to the patient 4.

The reference arrays 7, 8 and 9 can be located and tracked by an optical tracking system 6, which in the present example includes a stereoscopic camera array and electronic components and programs that enable a spatial location of the reference arrays 7, 8 and 9 to be determined. After calibration and/or registration (or in pre-calibrated systems), locating the reference arrays 7, 8 and 9 also enables the spatial position of the component to be determined relative to the respective reference arrays. For example, the position of the robot base 2, the functional element 16 or of a particular part of the body of the patient 4 to which the reference array 9 is fixed, may be determined from a positional location of the reference arrays 7, 8 and/or 9.

The tracking system 6 therefore forms a first tracking system which could also be referred to as an external tracking system. A second tracking system can be defined by the joint sensors 10', 12' and 14' of the robot 1. It is possible on the one hand to ascertain the position of the functional element 16 via the internal tracking system of the robot 1 (e.g., via the joint sensors 10', 12' and 14'), and on the other hand to ascertain the position of the functional element 16 using the external tracking system 6 via the position of the reference array 7. It is thus possible to make a redundant position determination using the two systems, and the corresponding position data can be relayed to a data processing and/or controlling unit 3, which typically forms a part of a medical navigation system.

It should also be noted that not only the position of the functional element 16 can be redundantly determined in this way. If, for example, the functional element 16 (which in this case can be a surgical pointer) is moved to a point on the patient, the location of which can also simultaneously be communicated to the tracking system 6 by the reference array 9, the position of this point can be determined both by the internal joint sensor tracking system of the robot 1 and by the external tracking system 6.

The data from the two position determinations are collected and processed, for example, in the controlling and/or data processing unit 3 (which can include a memory 3a and input device 3b), such as is explained below on the basis of FIG. 2. FIG. 1 also shows an arrow leading from the unit 3 to the robot 1 (to its base 2), which is intended to illustrate that the robot can be controlled by the unit 3 on the basis of the method described herein.

Figure 2:
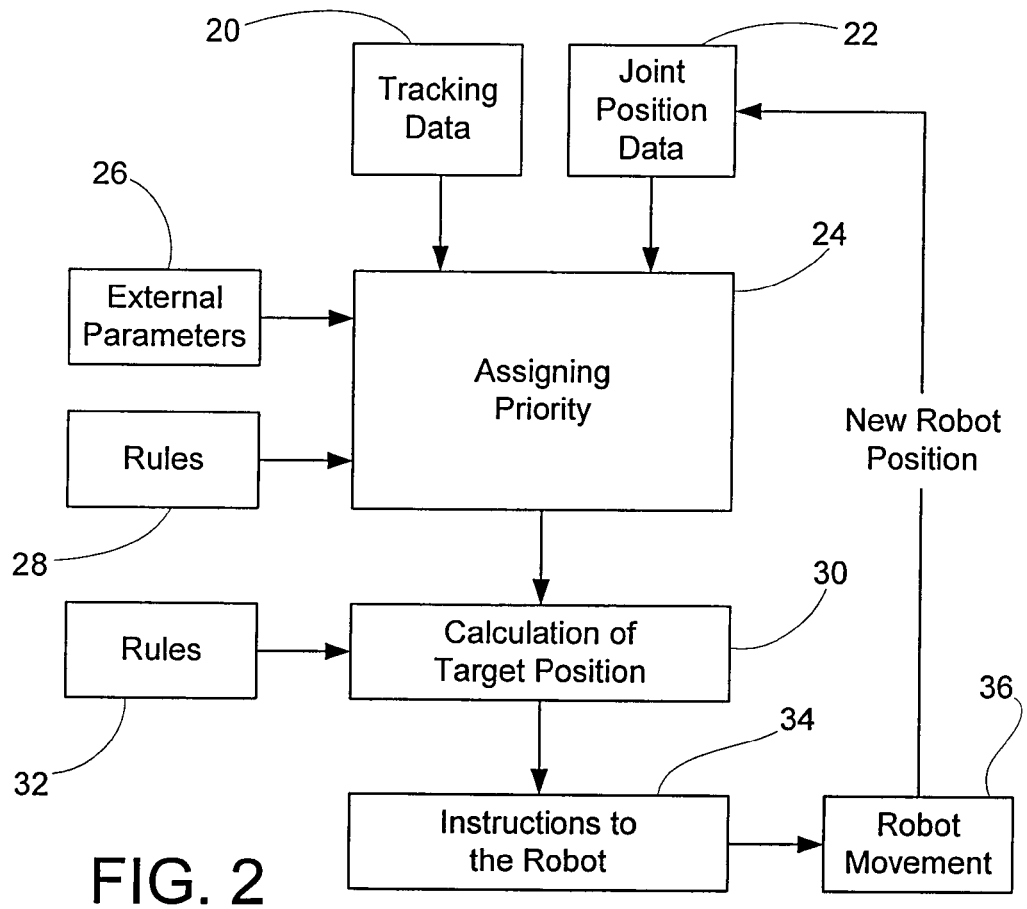
FIG. 2 is an exemplary flow diagram for determining the position and controlling the robot in accordance with the invention.

The aforementioned position determination, data processing and robot control is schematically shown as an exemplary flow diagram in FIG. 2. The sequence begins at block 20 with collecting tracking data from the tracking system 6 (the external tracking system) and at block 22, joint position data obtained from the joint sensors 10', 12' and 14' of the robot 1. At block 24, these position data are combined (e.g., in the controlling and data processing unit 3 shown in FIG. 1), and priorities are assigned on the basis of input variables, such as has been described in detail above. At blocks 26 and 28, external parameters and particular rules, for example, may be input as input variables to block 24. One example of an external parameter may be establishing that particular reference markers of the marker array 7 and/or 9 are significantly soiled and, therefore, can no longer provide good position data. The priority would then be shifted in favor of the joint sensor position data. One example of the rules on which the assigned priorities may be based could be the amount of time since the joint sensors were last calibrated. For example, the longer the time period since the last calibration, the more likely it will be that the reported positions include some error. The priority then would be shifted in favor of the data from the tracking system.

At block 30, a target position can be calculated using the assigned priorities. This target position can be the position of the part of the body that is to be treated using the robot. Alternatively, the target position can be some other position of interest, for example the position of the functional element 16. These positions can be determined both via the joint sensors 10', 12' and 14' and via the tracking system 6 by means of the reference array 7.

If the position of the part of the body to be treated is the target position, then at block 32 additional rules may be provided to block 30 to ascertain the target position. These rules can include, for example, rules pertaining to user inputs (e.g., confirmations, corrections, override specifications) or general rules for calculating the target position.

If the target position has been calculated by optimally utilizing all the information available, then at block 34 instructions can be provided to the robot, wherein the instructions cause the robot to move to a new position as indicated at block 36. This position can be a position approximate to the target or the target position itself, at which the robot performs its task.

Using this new robot position (from the internal position detection) and using new tracking data from the external tracking system, the process then can be continuously or intermittently repeated, so to as to provide optimum navigation assistance and/or position detection or robot control over the total period of treatment.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a position of an object, comprising:
   using first and second position detection devices to obtain first and second positions, respectively, of the object, said first position detection device being different from the second position detection device;
   assigning a first weight factor to the first position and a second weight factor to the second position, said first and second weight factors based on at least one input variable; and
   determining the position of the object from the combination of
   the first position and the first weight factor, and
   the second position and the second weight factor.

2. The method according to claim 1, wherein using the first and second position detection devices to obtain first and second positions includes obtaining the first and second positions for the same point in time.

3. The method according to claim 1, wherein the first and second weight factor are greater than 0% and less than 100%.

4. The method according to claim 1, wherein the at least one input variable describes a reliability and/or accuracy of the first and/or second position.

5. The method according to claim 1, wherein assigning based on at least one input variable includes using external parameters and/or predefined rules.

6. The method according to claim 1, wherein assigning based on at least one input variable includes using at least one of the following as the input variable:
  a distance measured between a medical device and a part of the patient's body;
  a time interval since the first and/or second position detection devices were last calibrated;
  a current detectability of a respective position detection device;
  a difference between the first and second positions;
  a ratio of the first or second weight factor with respect to a third weight factor of a third position detection device, wherein the third weight factor is constant; or
  an average or interim value of the first and second positions.

7. The method according to claim 1, wherein determining the position includes using control variables to determine the position of the object, said control variables including at least one of a user request, a user input, a user confirmation, a user intervention, or a user override.

8. The method according to claim 1, wherein assigning the first and second weight factor includes restricting the assigned weight factor to a particular time interval.

9. The method according to claim 1, wherein assigning the first and second weight factor includes recording the first and second weight factor.

10. The method according to claim 1, wherein the first position detection device is a medical manipulator, and the second position detection device is an optical or magnetic medical tracking system, and wherein the at least one input variable includes at least one of:
  a number of reference markings detected by the tracking system;
  a number of detected markings within a group or array of reference markings and/or the quality of detection;
  a difference between position data from at least two redundant joint position sensors of the medical manipulator;
  forces measured by force sensors of the medical manipulator;
  a difference between position data from the medical manipulator and the tracking system;
  a position of the tracking reference markings in the field of vision of the tracking system; or
  when a base of the manipulator is tracked by the tracking system, a distance and/or change in distance over time between the base and the medical device or part of the patient's body.

11. The method according to claim 10, wherein the medical manipulator is a medical or surgical jointed robot.

12. The method according to claim 10, further comprising using the determined position to control the medical manipulator.

13. The method according to claim 12, further comprising changing position input data for controlling the manipulator if the weight factor is changed.

14. The method according to claim 12, further comprising changing position input data for controlling the manipulator based on user intervention.

15. The method according to claim 12, further comprising changing position input data for controlling the manipulator when a difference between various detected positions or position data reaches or exceeds a threshold value.

16. The method according to claim 12, further comprising displaying the weight factor of the detected positions.

17. The method according to claim 1, wherein the object is at least one of a medical device or a part of a patient's body.

18. A computer program embodied on a non-transitory computer readable medium for determining a position of an object based on position data from a first and second position detection device, said first position detection device being different from the second position detection device, comprising:
  code that directs first and second position detection devices to obtain first and second positions, respectively, of the object;
  code that assigns a first weight factor to the first position and a second weight factor to the second position, said first and second weight factor based on at least one input variable; and
  code that determines the position of the object from the combination of
  the first position and the first weight factor, and
  the second position and the second weight factor.

19. A device for determining a position of an object, comprising:
  at least two different position detection devices for detecting first and second positions of the object,
  a controlling and data processing unit that includes a memory unit and/or input unit for at least one defined input variable, said controlling and data processing unit operative to
    assign a first weight factor to the first position and a second weight factor to
    the second position based on at least one input variable, and
    determine the position of the object from the combination of
    the first position and the first weight factor, and
    the second position and the second weight factor.

20. The device according to claim 19, wherein the controlling and data processing unit is operative to control a medical manipulator to move the medical device to the determined location.

21. The device of claim 20, wherein the medical manipulator is a medical robot.

22. A method for determining a position of an object, comprising:
  using first and second position detection devices to obtain first and second positions, respectively, of the object, said first and second position detection devices operative to obtain said first and second positions of the object independent of one another;
  assigning a first weight factor to the first position and a second weight factor to the second position, said first and second weight factors based on at least one input variable; and
  determining the position of the object from the combination of
  the first position and the first weight factor, and
  the second position and the second weight factor.

* * * * *